United States Patent
Eckenhoff

[11] Patent Number: 5,861,166
[45] Date of Patent: Jan. 19, 1999

[54] DELIVERY DEVICE PROVIDING BENEFICIAL AGENT STABILITY

[75] Inventor: James B. Eckenhoff, Los Altos, Calif.

[73] Assignee: ALZA Corporation, Palo Alto, Calif.

[21] Appl. No.: 129,558

[22] Filed: Sep. 30, 1993

Related U.S. Application Data

[63] Continuation of Ser. No. 909,504, Jul. 2, 1992, abandoned, which is a continuation-in-part of Ser. No. 667,937, Mar. 12, 1991, abandoned.

[51] Int. Cl.⁶ .................................................. A61K 9/20
[52] U.S. Cl. ........................ 424/422; 424/423; 424/427; 424/430; 424/434; 424/438
[58] Field of Search ................................ 424/422, 438, 424/423, 427, 430, 434

[56] References Cited

U.S. PATENT DOCUMENTS

| | | | |
|---|---|---|---|
| 3,845,770 | 11/1974 | Theeuwes | 128/260 |
| 3,865,108 | 2/1975 | Hartop | 128/260 |
| 3,916,899 | 11/1975 | Theeuwes et al. | 128/260 |
| 3,995,632 | 12/1976 | Nakano et al. | 128/260 |
| 4,002,173 | 1/1977 | Manning et al. | 128/296 |
| 4,063,064 | 12/1977 | Saunders et al. | 219/121 L |
| 4,088,864 | 5/1978 | Theeuwes et al. | 219/121 L |
| 4,111,202 | 9/1978 | Theeuwes | 128/260 |
| 4,111,203 | 9/1978 | Theeuwes | 128/260 |
| 4,200,098 | 4/1980 | Ayer et al. | 128/260 |
| 4,203,439 | 5/1980 | Theeuwes | 128/260 |
| 4,207,893 | 6/1980 | Michaels | 128/260 |
| 4,285,987 | 8/1981 | Ayer et al. | 427/3 |
| 4,320,759 | 3/1982 | Theeuwes | 128/260 |
| 4,327,725 | 5/1982 | Cortese et al. | 128/260 |
| 4,391,797 | 7/1983 | Folkman et al. | 424/19 |
| 4,526,938 | 7/1985 | Churchill et al. | 525/415 |
| 4,612,008 | 9/1986 | Wong et al. | 604/892 |
| 4,783,337 | 11/1988 | Wong et al. | 424/468 |
| 4,855,141 | 8/1989 | Eckenhoff et al. | 424/423 |
| 4,874,388 | 10/1989 | Wong et al. | 604/891.1 |
| 5,000,957 | 3/1991 | Eckenhoff et al. | 424/438 |
| 5,023,088 | 6/1991 | Wong et al. | 424/473 |
| 5,034,229 | 7/1991 | Magruder et al. | 424/422 |
| 5,045,082 | 9/1991 | Ayer et al. | 604/892.1 |
| 5,128,145 | 7/1992 | Edgren et al. | 424/439 |
| 5,137,727 | 8/1992 | Eckenhoff | 424/426 |

FOREIGN PATENT DOCUMENTS

| | | |
|---|---|---|
| 0246819 | 11/1987 | European Pat. Off. . |
| 0374120 | 6/1990 | European Pat. Off. . |
| 2189995 | 11/1987 | United Kingdom . |
| 9200728 | 1/1992 | WIPO . |

*Primary Examiner*—Raj Bawa
*Attorney, Agent, or Firm*—Pauline Ann Clarke; Steve F. Stone; Mary Ann Dillahunty

[57] ABSTRACT

This invention relates to fluid-imbibing delivery devices for delivering a beneficial agent to a biological environment of use. In particular, the devices include a rigid housing defining an internal compartment comprising a substantially impermeable first wall section and a second wall section permeable to fluid in the environment of use. The first wall section may be shape-retaining, with exit means and an open end, and extend for at least 85% of the entire length of the device to define the internal compartment.

14 Claims, 2 Drawing Sheets

FIG.1
FIG.2
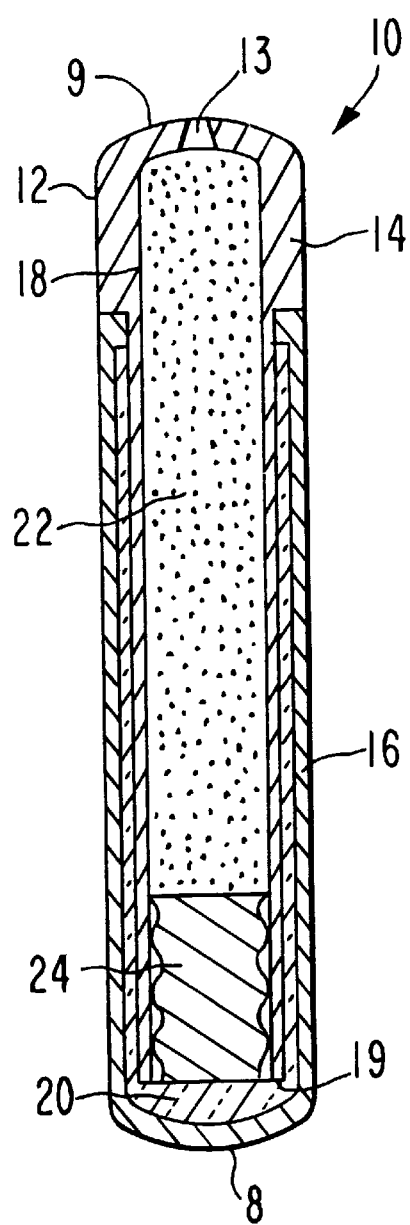
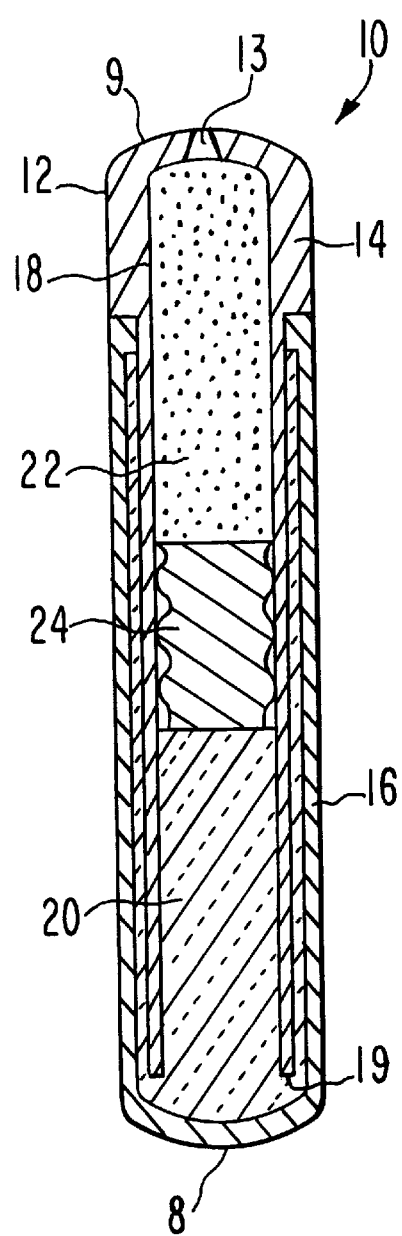

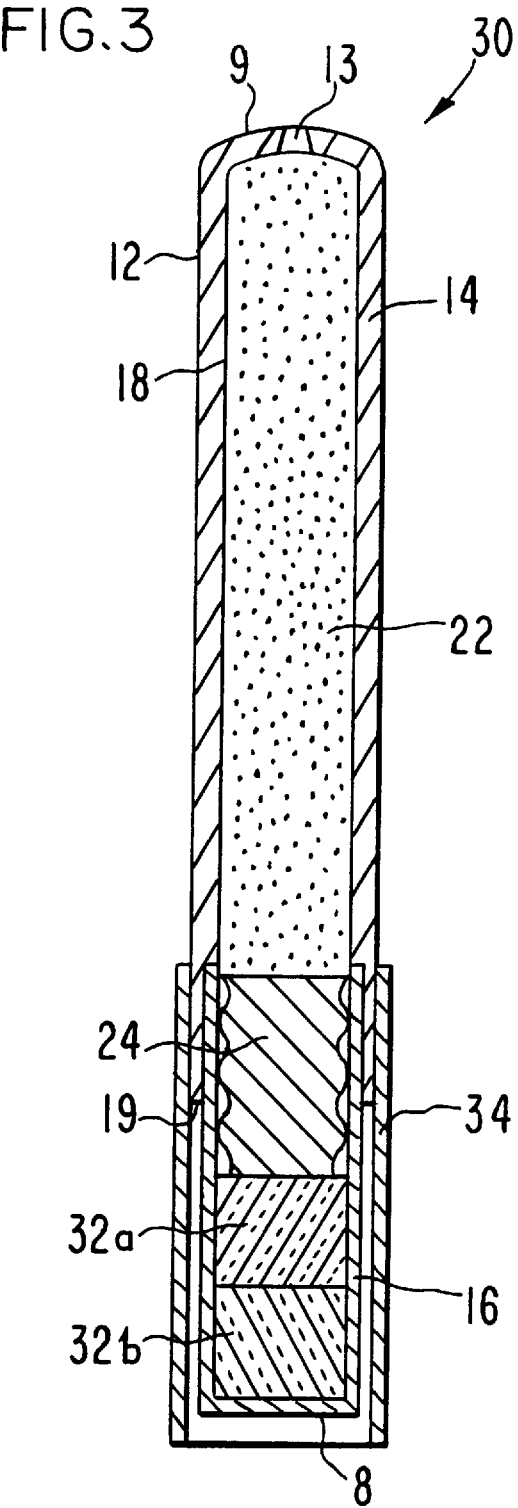

DELIVERY DEVICE PROVIDING BENEFICIAL AGENT STABILITY

This application is a continuation of application Ser. No. 07/909,504 filed Jul. 2, 1992, now abandoned, and benefit of the filing date of said earlier filed application is claimed under 35 U.S.C. §120, which application is a continuation-in-part of application Ser. No. 07/667,937, filed Mar. 12, 1991, now abandoned.

FIELD OF THE INVENTION

This invention relates to an active agent delivery device. More particularly, the invention relates to a delivery device that is robust and resistant to transient mechanical forces while being space- and beneficial agent stability-efficient.

BACKGROUND OF THE INVENTION

Delivery devices for administering a beneficial agent to a biological fluid environment of use are known in the prior art. Representative examples of various types of delivery devices are disclosed in U.S. Pat. Nos. 3,845,770; 3,916,899; 3,995,632; 4,111,202; 4,111,203; 4,203,439; 4,327,725; and 4,612,008; all of which are incorporated herein by reference. The delivery devices described in the above patents operate successfully for their intended use and they can deliver many beneficial agents for their intended effects. However, it has been observed that their use can be limited because they lack the necessary elements to deliver beneficial agents that are sensitive to fluids and to fluids containing biological gases. Their use may be limited because beneficial agents that are sensitive to such aqueous biological fluids or to other fluids external to the delivery device may be adversely affected by fluids that enter the device and contact the beneficial agents during operation of the device. Examples of such fluid-sensitive agents include proteins, peptides, and hormones. Moreover, the prior art devices lack the necessary means for their use as implant devices for dispensing such sensitive agents to a biological fluid-rich environment of use.

To overcome the limitations associated with the prior art delivery devices, a delivery device was developed and is described and claimed in U.S. Pat. No. 5,034,229. This delivery device comprises a compartment, one portion of which is impermeable to fluid and contains a fluid-sensitive drug protected from a fluid environment and a second portion of which is permeable to fluid and contains an expandable driving member for administering the drug to the fluid environment of use. The system has been found to be particularly useful as an implant in livestock for delivering a fluid-sensitive drug over a broad range of dosage delivery rates according to a predetermined time-release pattern.

Although in vitro tests and in vivo tests on isolated animals indicated satisfactory system performance, in vivo tests under field conditions of the delivery device of U.S. Pat. No. 5,034,229 in livestock demonstrated an undesirably high failure rate, either by failing to deliver the beneficial drug at the desired rates or by failing to deliver the required dosage of the drug or by the fluid-sensitive drug in the device coming into contact with fluid prematurely and becoming adversely affected prior to its delivery into the fluid environment of the host animal. The discrepancy between in vivo tests on isolated animals and on animals under field conditions was totally unexpected, not readily explained, and could adversely affect the commercialization of the delivery device.

It was discovered that the failure of the devices of U.S. Pat. No. 5,034,229 under field conditions was attributable to damage to the portion of the compartment containing the expandable driving member or damage to the junction between the permeable and impermeable portions of the compartment as a result of radially applied transient mechanical forces, which forces are the result of such actions as the implant procedure itself; behavior patterns of the host animals, such as animal-to-animal interaction which is often violent, and collisions of the animals into guardrails of pens or other structures; and miscellaneous in vivo forces which act upon the implanted delivery device. It was also discovered that the frequency of failure could be greatly reduced if these delivery devices were rendered more robust and resistant to such transient mechanical forces in a manner that does not interfere with delivery of the protected beneficial agent at a controlled rate.

Accordingly, an improvement to the delivery device was developed and is described and claimed in PCT patent publication WO 92/00728 to Magruder et al. for Delivery Device with a Protective Sleeve. This delivery device is similar to that of U.S. Pat. No. 5,034,229 except that it additionally has a protective sleeve means extending from the first wall section of the housing to cover and protect the second wall section of the housing and the junction of the first and second sections.

While the addition of a protective sleeve has provided substantial protection to the device, resulting in reduced failures of the system and increased effectiveness, at the same time it has added extra weight and bulk to the system, which is undesirable in many types of use, such as an implant device. Also, an additional part or piece, the sleeve, is now required and an additional step in the manufacture of the device is now necessary, both of which add to the cost of the device.

Therefore, it is still desirable to provide an implantable delivery device that is of a smaller size and lighter weight while also being robust and resistant to mechanical forces in vivo.

Another disadvantage recently discovered with the devices of both U.S. Pat. No. 5,034,229 and WO 92/00728 is that certain stable and resorbable somatotropin formulations to be delivered are osmotically active, having the same osmotic activity as a saturated solution of sodium chloride. At the same time, the osmotic permeability to water of the substantially impermeable reservoir wall surrounding the formulation is in fact finite. The combination of these two characteristics results in absorption of some water through the reservoir wall and dilution and some inactivation of somatotropin inside the reservoir. In vitro and in vivo testing results from prior art devices have demonstrated up to 20–25% dilution of the fluid-sensitive beneficial agent formulation at 4–5 weeks of delivery.

Accordingly, it is desirable to provide a delivery device that is not only robust and resistant to mechanical forces in vivo but provides improved stability for the benficial agent formulation in vivo; that is, it does not cause the dilution and inactivation of an active agent to be delivered by the device.

SUMMARY OF THE INVENTION

Therefore, it is an object of the present invention to provide a delivery device that delivers a fluid-sensitive active agent without diluting or inactivating the agent prior to delivery into the environment of use.

It is another object of the invention to provide a delivery device that is robust and resistant to mechanical forces in vivo.

It is a further object of the invention to provide a delivery device that is robust and resistant to mechanical forces while being of a small size suitable for implantation into an animal.

These and other objects are met by the present invention which provides a fluid-imbibing delivery device comprising (a) a rigid housing enclosing an internal compartment, the housing having
  (i) a shape-retaining first wall section having exit means and an open end;
  (ii) an osmotically active expandable driving member surrounding and enclosing the open end and an extensive portion of the vertical sides of the first wall section; and
  (iii) a fluid-permeable second wall section surrounding and enclosing the expandable driving member;
(b) a beneficial agent formulation in a portion of the internal compartment adjacent to the exit means; and
(c) optionally, a fluid-impermeable partition layer between the beneficial agent formulation and the expandable driving member.

The present invention is also directed to a method for using the above delivery device to deliver an active agent to an environment of use.

BRIEF DESCRIPTION OF THE DRAWINGS

FIG. 1 is a cross-sectional view of one embodiment of the delivery device of the invention, prior to placement in an environment of use.

FIG. 2 is a cross-sectional view of the delivery device of FIG. 1 after it has been activated and has delivered active agent for a period of time.

FIG. 3 is a cross-sectional view of a prior delivery device as described in WO 92/00728, having a protective sleeve.

DETAILED DESCRIPTION OF THE INVENTION

In the following discussion, like reference numerals refer to like elements in the figures.

FIG. 1 depicts in cross-sectional view a presently preferred embodiment of the delivery device according to the present invention. Delivery device 10 of FIG. 1 comprises a rigid housing 12 formed of a first wall section 14 and a second wall section 16, both of which retain their shapes. Housing 12 surrounds and defines an internal compartment 18. Delivery device 10 has at least one exit passageway 13 for delivering a beneficial agent formulation from device 10. Optionally, the exit passageway can be occluded with a material that is discharged, leaches or erodes during the time of use. In FIG. 1, housing 12 comprises a dome-shaped rear end 8 and a similar dome-shaped lead end 9 for aiding in placing delivery device 10 in an animal host. In an embodiment not shown, delivery system 10 can be manufactured with a pair of flat ends 8 and 9. The term "lead end", as used herein, generally denotes the end from which beneficial agent is released from the device. In use, either the lead end or the rear end may be implanted first. First wall section 14 defines lead end 9, it forms passageway 13 and it extends for substantially the entire length of device 10 to define internal compartment area 18 which contains a beneficial agent formulation 22. First wall section 14 at its end distant from lead end 9 defines and forms an open end 19. Surrounding and enclosing open end 19 and an extensive portion of the vertical walls of first wall section 14 is expandable driving member 20, for expanding and for occupying space in compartment 18 for delivery of a beneficial agent formulation from delivery device 10. Second wall section 16 surrounds and encloses expandable driving member 20.

Compartment 18 comprises a beneficial agent formulation 22. Compartment 18 further optionally, and preferably, comprises a partition layer 24 which is positioned between the beneficial agent formulation 22 and the expandable driving member 20 at the open end 19 of first wall section 14. Partition layer 24, in a presently preferred embodiment, comprises a composition that is substantially impermeable to the passage of fluid, and it serves to restrict the passage of fluid present in the expandable driving member into the beneficial agent formulation. It operates to essentially maintain the integrity of the beneficial agent layer and the driving member layer. Partition layer 24 acts also to insure that the expanding driving force generated by the expandable driving member 20 is applied directly against the beneficial agent formulation 22.

In operation, as the expandable driving member 20 absorbs and imbibes fluid through second wall section 16 from the environment of use, it expands at the only point where expansion is possible in the rigid device, that is, at open end 19 of first wall section 14. The expandable member pushes against partition layer 24, causing it to slide inside compartment 18. As the driving member continues to expand into compartment 18, partition layer 24 moves towards exit passageway 13, as illustrated in FIG. 2, pushing the beneficial agent formulation 22 through passageway 13 for maximizing the delivery of the beneficial agent to a biological environment of use, such as livestock.

FIG. 2 illustrates the dispensing device 10 of FIG. 1 after activation of the device by placement in the environment of use. FIG. 2 shows device 10 after a portion, approximately half, of the beneficial agent formulation 22 has been released to the environment. Expandable driving member 20 has expanded into the internal compartment 18 from open end 19, pushing partition layer 24 up into the compartment as well, which has caused beneficial agent to be displaced out through the exit passageway 13 into the environment.

First wall section 14, which surrounds the internal space of compartment 18 initially occupied by the beneficial agent formulation 22 and the partition layer 24, comprises a composition that does not adversely affect the beneficial agent or other ingredients in delivery device 10, the host, or the like. First wall section 14 comprises a composition comprising means that substantially limits or prevents the passage of an external fluid into device 10. The phrase, "substantially limits or prevents," as used herein, indicates the osmotic permeability coefficient is less than $3.7 \times 10^{-7}$ cm.mil/atm.hr or the water vapor transmission rate is less than 11 g.mil/100 in$^2$/24 hr at 38° C. Typical impermeable compositions for forming first wall section 14 are, for example, vinylidene chloride copolymers and terpolymers such as vinylidene chloride-vinyl chloride copolymer, vinylidene chloride-acrylonitrile copolymer, vinylidene chloride-styrene copolymer, and vinylidene chloride-vinyl chloride-acrylonitrile terpolymer; acrylonitrile polymers such as acrylonitrile-methyl vinyl ether copolymer, acrylonitrile-styrene copolymer, acrylonitrile-butadiene-styrene terpolymer, and the like; halogenated polymers such as chlorinated polyether, polytetrafluoroethylene, polychlorotrifluoroethylene, tetrafluoroethylene and hexafluoropropylene copolymer, polyvinylfluoride, polyvinylchlorobuteral, plasticized polyvinylidene chloride, and the like; nylon; polyamide-imide; polyarylether; polysulfone; polycarbonate; polyurethane; high density polyethylene; polyvinylchloride-acrylic copolymer;

polycarbonate-acrylonitrile-butadiene-styrene; glass; bakelite; melamine; polystyrene; polyacrylate; stainless steel and stainless steel mesh; and the like. Polycarbonate and polysulfone are presently preferred. The polymers are known in the *Handbook of Common Polymers,* by Scott and Roff, CRC Press, Cleveland Rubber Co., Cleveland, Ohio.

Because of the transient mechanical forces exerted on the device 10 after it has been implanted in a host animal, it is necessary that at least the first wall section 14 be comprised of a material of a strength sufficient to withstand transient mechanical forces of at least about 2 $kg_f$ and preferably of at least about 6 $kg_f$ of force. Usually, a material having a minimum tensile strength at yield of about 9,000 psi is acceptable for use in the present invention. The tensile strength may be lower, in which case the wall is thicker to provide the necessary strength.

To further reduce or limit permeability of the compositions making up first wall section 14, impermeable particulate fillers known to the industry, such as, for example, titanium dioxide and mica flakes, or homogeneous polymer alloys and barriers are within the scope of this invention and can be used to form first wall section 14.

Because expandable driving member 20 operates by the imbibition of external fluid, second wall section 16 in at least a portion that is adjacent to expandable member 20 must comprise a composition that is permeable to the passage of external fluids such as water and biological fluids, and is substantially impermeable to the passage of beneficial agents, osmopolymers, osmagents, and the like. Typical compositions comprising semipermeable materials for forming wall 16 are known in the art. In one presently preferred embodiment, they are a member selected from the group consisting of a cellulose ester, a cellulose ether and a cellulose ester-ether. These cellulosic polymers have a degree of substitution, D.S., on the anhydroglucose unit from greater than 0 up to 3, inclusive. By "degree of substitution" or "D.S" is meant the average number of hydroxyl groups originally present on the anhydroglucose unit comprising the cellulose polymer that are replaced by a substituting group. Representative fluid-permeable materials are discussed in U.S. Pat. No. 4,874,388, for example, the entire disclosure of which is incorporated herein by reference.

First wall section 14 and second wall section 16 optionally comprise a nontoxic plasticizer. Representative plasticizers suitable for forming wall 14 and wall 16 include plasticizers that lower the temperature of the second-order phase of transition or the elastic modulus of a composition. Also, the plasticizers increase the workability of wall 14 and wall 16 and their flexibility. Plasticizers operable for the present purpose include straight-chain and branched-chain plasticizers, cyclic plasticizers, acrylic plasticizers and heterocyclic plasticizers. Representative plasticizers are well known in the art, examples of which are disclosed in U.S. Pat. No. 4,874,388.

Housing 12, comprising wall sections 14 and 16, is nontoxic, biologically inert, nonallergenic and nonirritating to body tissue, and it maintains its physical and chemical integrity; that is, housing 12 does not erode or degrade in the environment of use during the dispensing period. It is within the scope of the invention that the housing be insoluble only during the period of intended use and can thereafter dissolve away in the environment of the device. Thus, a dispenser is here contemplated which is unaffected by its environment, solubility-wise, at the situs of use or which, alternatively, is only slightly soluble during the period of intended use, such that once its active agent content has been removed it will then dissolve or erode away leaving no objectionable residue or empty container at the situs of use. Additionally, housing 12, comprised of wall sections 14 and 16, is rigid; that is, it retains its shape and is inflexible so that it does not bend or otherwise deform as a result of transient mechanical forces.

Delivery device 10 comprises a beneficial agent formulation 22 that produces a desired and useful result when administered to a warm-blooded animal, including humans and farm animals. The term "beneficial agent formulation", as used herein, comprises the active agent to be delivered, generally in a carrier substance and with or without additional inert ingredients. The pharmaceutically acceptable carrier useful herein may comprise more than one ingredient, such as, for example, a buffer, a viscosity-regulating vehicle, a surfactant, dyes, a permeation enhancer, proteinase inhibitors, or other formulation ingredients and additives, as are known in the art.

The beneficial agent in formulation 22 is useful in one embodiment for increasing the rate of growth and the efficiency of feed utilization in equine, bovine and swine. The beneficial agent in another embodiment is useful for controlling estrus and ovulation in the course of breeding farm animals for commercial purposes, for effecting contraception and for producing an anabolic response associated with the inhibition of estrus. Beneficial agent in another embodiment is a drug useful for producing a therapeutic effect. The beneficial agent in yet other embodiments comprises agents that act at synaptic and neuroeffector sites, agents acting on the central nervous system, autocoids, anti-inflammatory agents, analgesics, antipyretic agents, cardiovascular agents, and the like.

The terms "active agent", "beneficial agent" and "drug" are used interchangeably herein and refer to an agent, drug, compound, composition of matter or mixture thereof which provides some therapeutic, often beneficial, effect. Representative beneficial agents that can be administered by delivery device 10 include pharmacologically active peptides and proteins, anabolic hormones, growth promoting hormones, hormones related to the endocrine system comprising porcine growth promoting hormone, bovine growth promoting hormone, equine growth promoting hormone, ovine growth promoting hormone, human growth promoting hormone, growth promoting hormones derived by extraction and concentration from pituitary and hypothalmus glands, growth promoting hormones produced by recombinant DNA methods, bovine growth promoting hormone as described in *Nucleic Acid Res.,* 10:7197 (1982), ovine growth promoting hormone as described in *Arch. Biochem. Biophys.,* 156:493 (1973), and porcine growth promoting hormone as described in *DNA,* 2:37 (1983). The polypeptides also comprise growth hormone, somatropin, somatotropin, somatotropin analogues, modified porcine somatotropin, modified bovine somatotropin, derivatives of somatotropin including both porcine and bovine somatotropin derivatives, somatomedin-C, gonadotropic releasing hormone, follicle stimulating hormone, luteinizing hormone, LH-RH, growth hormone releasing factor, gonadotropin releasing factor, insulin, colchicine, chorionic gonadotropin, oxytocin, somatotropin plus an amino acid, vasopressin, adrenocorticotrophic hormone, epidermal growth factor, prolactin, somatostatin, somatotropin plus a protein, cosyntropin, lypressin, polypeptides such as thyrotropin releasing hormone, thyroid stimulating hormone, secretin, pancreozymin, enkephalin, glucagon, endocrine agents secreted internally and distributed in an animal by way of the bloodstream, and the like.

The amount of active or beneficial agent employed in the delivery device of the invention will be that amount necessary to deliver a therapeutically effective amount of the agent to achieve the desired result at the site of delivery. In practice, this will vary widely depending upon the particular agent, the site of delivery, the severity of the condition, and the desired therapeutic effect. Thus, it is not practical to define a particular range for the therapeutically effective amount of active agent incorporated into the device. Beneficial agents and their dosage unit amounts are known to the prior art in *The Pharmacological Basis of Therapeutics*, by Gilman, Goodman, Rall and Murad, 7th Ed., (1985), MacMillan Publishing Co., NY; in *Pharmaceutical Sciences*, Remington, 17th Ed., (1985), Mack Publishing Co., Easton, Pa.; and in U.S. Pat. No. 4,526,938. Other useful beneficial agents are discussed in U.S. Pat. No. 4,874,388.

As used herein, the term "therapeutically effective amount" refers to the amount of the active agent needed to effect the desired therapeutic result.

The expandable driving member 20 initially surrounded by second wall section 16 and operable for pushing the beneficial agent composition 22 from delivery device 10 comprises, in a presently preferred embodiment, an osmopolymer. The osmopolymers interact with water and aqueous biological fluids and swell or expand to an equilibrium state. The osmopolymers exhibit the ability to swell in water and to retain a significant portion of the imbibed and absorbed water within the polymer structure. The expandable driving member 20 in another preferred embodiment comprises an osmagent. The osmagents are known also as osmotically effective solutes and they are also known as osmotically effective compounds. The osmotically effective solutes that can be used for the purpose of this invention include inorganic and organic compounds that exhibit an osmotic pressure gradient across a semipermeable, i.e. a fluid-permeable, wall. The expandable driving member 20 in yet another preferred embodiment comprises an optional osmagent dispersed within the osmopolymer. The osmagent or osmopolymer can be in any suitable form such as particles, crystals, pellets, granules, and the like, when pressed into a layer and surrounded by wall section 16. Osmagents and osmopolymers are known to the art in U.S. Pat. Nos. 3,865,108, 4,002,173, 4,207,893, 4,327,725 and 4,612,008, for example. Other expandable driving members which may be useful are known to the art, examples of which are presented in U.S. Pat. No. 5,023,088, for example.

Partition layer 24, positioned between the beneficial agent composition and the expandable driving member, is a means for maintaining the separate identity of the beneficial agent composition and the driving member, for transmitting the force generated by the driving member against the beneficial agent composition, and for substantially restricting the passage of fluid between the beneficial agent composition and the driving member. Representative materials useful as a partition layer 24 are known to the art in, for example, U.S. Pat. No. 4,874,388.

The terms "exit means" and "exit passageway", as used herein, comprise means and methods suitable for the metered release of the beneficial agent 22 from compartment 18 of delivery device 10. The exit means 13 includes at least one passageway, orifice, or the like, through first wall section 14 for communicating with compartment 18. The expression "at least one passageway" includes aperture, orifice, bore, pore, porous element through which the agent can migrate, hollow fiber, capillary tube, porous overlay, porous insert, and the like. The expression also includes material that is discharged, erodes or is leached from the wall in the fluid environment of use to produce at least one passageway in delivery device 10. Representative materials suitable for forming at least one passageway, or a multiplicity of passageways, include an erodible poly(glycolic) acid or poly(lactic) acid member in the wall; a gelatinous filament; poly(vinyl alcohol); leachable materials such as fluid-removable pore-forming polysaccharides, salts, or oxides; erodable or dischargable materials such as natural and synthetic waxes; and the like. The expression includes structural characteristics that concentrate stress at a precise point in the wall so that only a small amount of force will induce breakage in the wall, yielding a passageway through the wall from compartment 18 to the outside of the device. A passageway or a plurality of passageways can be formed by leaching a material such as sorbitol, lactose and like water-soluble solids from the wall. A passageway or passageways can be formed by the discharge, as a result of the pressure created by the expandable member for example, of a material such as a wax. The means or passageway can have any shape such as round, triangular, square, elliptical, and the like, for assisting in the metered release of beneficial agent from delivery device 10. Delivery device 10 can be constructed with one or more passageways in spaced-apart relations or more than a single surface of a dosage form. Passageways and equipment for forming passageways are disclosed in U.S. Pat. Nos. 3,845,770; 3,916,899; 4,063,064; and 4,088,864. Passageways formed by leaching are disclosed in U.S. Pat. Nos. 4,200,098 and 4,285,987.

Delivery device 10 can be manufactured by standard manufacturing techniques. In one process, the first wall section 14 and the second wall section 16 are independently injection molded or extruded into the desired shape. Then, the first wall section 14 is filled with the beneficial agent composition 22, and the partition layer 24 is added thereto in layered arrangement. The expandable driving member is formed by repeatedly dipping, with intervening drying periods, the filled and partition-plugged first wall section 14 into a suspension of the desired osmopolymer, osmagent or mixture of the two, to the desired height from open end 19 up the sides of wall section 14, until a layer of desired thickness of the driving member is formed. Alternatively, the driving member composition is sprayed onto the first wall section 14 to the desired thickness. Then, the second wall section 16 is fitted over the first wall section 14 and driving member 20. In an alternative method of manufacture, the material of the driving member is molded into a cup that fits into the sides and bottom of the second wall section 16, and the second wall section 16 together with the driving member 20 is then fitted over the first wall section 14. The union of the two wall sections can be effected by having the opened end of the second wall section 16 enlarged for slidably receiving the end of the first wall section 14 in mated relation to form an essentially fluid-tight union. In another embodiment, the opened end of the first wall section is made smaller than the end of the second wall section, and the smaller end of the first wall section is placed in the non-enlarged end of the second wall section to form a closed system. The two wall sections at their junction are optionally heat sealed, adhesive sealed, solvent sealed, ultrasonically sealed, radiofrequency sealed, or spin welded, also known as friction heating to weld. Then, at least one exit passageway 13 is drilled in the lead end 9 of the manufactured assembly. Alternately, the exit passageway can be preformed, such as during the injection molding of first wall section 14. Optionally, a passageway is drilled or preformed in the wall and sealed with a break-off tab that is broken open, or cut open, or the like, at the time of use to connect through the passageway the beneficial agent composition 22 with the exterior of delivery device 10. Or, the drilled or preformed passageway is sealed by a material that is discharged, leaches, erodes, or dissolves, for example, in the environment of use.

In one embodiment of delivery device 10 as illustrated in FIGS. 1 and 2, the device is manufactured as an implant comprising a body length of about 39.5 mm and diameter of about 7 mm for containing and delivering approximately 280 μL of beneficial agent, in contrast with the implant device of WO 92/00728 which has a body length of about 50 mm and diameter of about 5 mm for containing and delivering the same amount of beneficial agent. The difference in length is attributable to the placement of the expandable driving member in the present invention as a relatively thin layer surrounding an extensive portion of the vertical sides of the first wall section and with a relatively thin layer enclosing the open end of the first wall section, whereas the driving member in the previous device is present as tablets extending below the open end of the first wall section.

In the implant of the present invention, there is an extensive overlap of the expandable driving member and of the second wall section with the first wall section. Because the driving member is distributed along the sides of the first wall section, it is not necessary for the driving member and the second wall section to extend appreciably below the open end of the first wall section. As a result, the first wall section, having a high tensile strength, extends for substantially the entire length of the implant. This gives added strength and stability to the device so that it is not easily damaged or broken apart as a result of the transient mechanical forces that are applied to the device during the period of in vivo exposure to the environment of use. Thus, a protective sleeve such as that of WO 92/00728 is not necessary in order to provide protection and proper functioning of the device in the environment.

The extensive overlap of the expandable driving member and of the second wall section with the first wall section also provides stability to the fluid-sensitive beneficial agent within the first wall section. This is accomplished by the reduction in activity (vapor pressure) of imbibed fluid in the solution of the expandable driving member formed between the first and second wall sections as outside fluid is imbibed through the second wall section. The activity gradient between fluid in the driving member and the beneficial agent formulation existing across the first wall section is reduced and preferably eliminated by the selection of osmagent in the driving member. Fluid is then prevented from being drawn into the fluid-sensitive osmotically active beneficial agent formulation (such as certain presently preferred somatotropin formulations) into the internal compartment. For this reason, the expandable driving member in a particularly preferred embodiment of the invention is selected from osmagents or osmopolymers containing osmagents. Osmagents can include, for example, sodium chloride, sodium acetate, calcium chloride, and other inorganic compounds that act in combination to be a driving member and to simultaneously reduce the activity (vapor pressure) of fluid between the first and second wall sections.

By "extensive overlap" and "extensive portion" are meant an overlap or portion where at least about one-half and preferably at least about two-thirds, more preferably at least about 80%, of the length of the vertical sides of the first wall section is surrounded by the expandable driving member and the second wall section.

The device of WO 92/00728 is illustrated, for comparison with the present invention, in FIG. 3. In FIG. 3, delivery device 30 comprises housing 12 having a rear end 8, a lead end 9, a first wall section 14 with an opened end 19, a second wall section 16, an internal compartment 18, a beneficial agent formulation 22 in a portion of internal compartment 18, an exit passageway 13, two expandable driving members 32*a* and 32*b* in a portion of internal compartment 18, a partition layer 24 between the beneficial agent formulation 22 and the expandable driving members 32*a* and 32*b*, and a protective sleeve 34 which is joined with first wall section 14 at a position over the junction of wall sections 14 and 16 and which surrounds second wall section 16. The expandable driving members 32*a* and 32*b* are layered tablets which extend below the beneficial agent formulation and the partition layer. The prior devices of U.S. Pat. No. 5,034,229 are similar to device 30, except that they do not include a protective sleeve 34.

The delivery device of the present invention can be manufactured for delivering numerous beneficial agents, including drugs, at a controlled rate to a presently preferred biological environment of use such as warm-blooded animals, including humans; ruminants, such as bovines and sheep; porcines, such as hogs and swine; horses; and the like. The delivery devices provide for high loading of a beneficial agent and for its improved delivery in beneficially effective amounts over time while providing resistance to transient mechanical forces. It is to be understood that the delivery devices can take a wide variety of shapes, sizes and forms adapted for delivering beneficial agents to environments of use. For example, the devices manufactured as delivery devices can be used for dispensing a beneficial agent in the anal-rectal passageway, in the cervical canal, as an artificial gland, in the vagina, as a subcutaneous implant, and the like. The delivery devices can be used in hospitals, nursing homes, outpatient clinics, sickrooms, veterinary clinics, farms, zoos, and other environments of use.

One embodiment of the invention pertains to a method for delivering a beneficial agent such as a drug to a human or an animal. The method comprises placing a delivery device, appropriately shaped, sized and adapted (such as an implant, for example), into the human or animal, into a muscle or an internal or body cavity or subcutaneously under the skin of an ear or limb, for example. The method comprises the steps of: (a) admitting into an animal a delivery device of the present invention; (b) allowing fluid to be imbibed through the semipermeable second wall section of the delivery device for causing the expandable driving member to expand and push against the beneficial agent formulation; and (c) delivering the beneficial agent formulation from the delivery device by the expandable member increasing in volume at a controlled rate, thereby pushing the beneficial agent formulation to be delivered in an effective amount through the exit orifice to the animal over a prolonged period of time.

Where the device is an implant, the implant can be implanted into receiving tissue using an implanter. Generally, an implanter comprises a tubular member with a central longitudinal axial bore, a pointed, elongated, annular concavely beveled implanting end and an implant-charging end. The implanting end and the charging end communicate through a bore. A plunger adapted to be removably inserted in the bore is designed for slidable movement therein for applying the necessary force for implanting the implant. Also, the implant can be surgically implanted in the muscle or other tissue of an animal.

EXAMPLE 1

A delivery device manufactured in the shape of an implantable delivery device as illustrated in FIG. 1 is manufactured as follows.

First, a lead, impermeable first wall section is prepared by adding polycarbonate (Lexan® HP 1, General Electric) to a hopper dryer and drying the polymer at 250° F. for 4 hours. The dry polymer is then fed into the hopper of an injection molder with a mold designed with an orifice (exit passageway) in place, and the first wall section is injection molded into a shape as illustrated in FIG. 1. Next, the orifice channel is sealed with wax in the following manner. First, a 50/50 blend of microcrystalline wax 180M and microcrystalline wax X145A is melted and heated and held to 105°–115° C. The lead end (with the orifice channel) of the first wall section is dipped into the melted wax blend for 20 seconds, then removed from the melted wax and cooled for at least 20 seconds, and the excess wax is wiped off.

The semipermeable second wall section is prepared by blending a 85/15 ratio blend of cellulose acetate butyrate 500 polymer and tributyl citrate plasticizer in a Hobart® mixer for 5 minutes. The blend is then fed into an injection molder and molded into the second wall section having a shape as illustrated in FIG. 1 and a thickness of 0.020 inches.

An expandable driving member in the shape of a cup is prepared as follows. The components [64.5 wt % NaCl, 20 wt % N-10 poly(ethylene oxide) of molecular weight 100,000, and 15 wt % poly(ethylene glycol) of molecular weight 20,000] are blended in a Hobart mixer for 20 minutes at low speed. The homogeneous blend is pressed into 0.6 cm tablets capable of being gravity-fed into an Arburg® injection molder. The driving member cups are formed from the tablets by injection molding at 149° C. and $6.5 \times 10^3$ k$P_a$. The molded cups have a side wall thickness of 0.020 inches and a bottom wall thickness of 0.060 inches.

The elastomeric partition layer or piston is prepared by injection molding Santoprene®, a thermoplastic elastomer, into a four-ribbed piston. Then, the piston is lubricated with silicone medical fluid 1000 cs to facilitate movement of the piston inside the device.

The delivery device is assembled by first filling the substantially fluid-impermeable first wall section with a beneficial agent formulation at 40° C., wherein the formulation comprises 33.33 wt % (weight percent) porcine somatotropin, 4.53 wt % sodium phosphate monobasic, 28.47 wt % water, 33.0 wt % glycerol, and 0.67 wt % Tween-80. Then, the lubricated elastomeric piston is inserted on top of the beneficial agent formulation to be flush with the open end of the impermeable first wall section. Then, the cup formed of the expandable driving composition is fitted inside the semipermeable second wall section, and the semipermeable second wall section, with the expandable driving composition, is placed at its open end over the open end of the first wall section subassembly until the first wall section is almost completely inserted. Next, moisture-cured cyanoacrylic adhesive is dropped into the remaining exposed surface of the junction, and the members are fully inserted and then twisted to effect a sealed delivery device.

EXAMPLE 2

Following the procedures of Example 1, the first wall section is molded from a concentrate of polycarbonate and $TiO_2$ with neat polymer 1:1. The $TiO_2$ is used as an inert filler to reduce water permeability of the neat polycarbonate used in Example 1. The remainder of the device, composition and structure are manufactured as described in Example 1. The reduced permeability of the first wall section due to the inert filler and the reduced vapor pressure of water in the driving member surrounding the first wall section is found to stabilize the fluid-sensitive beneficial agent formulation during the delivery period.

The novel devices of this invention use means for the obtainment of precise release rates in the environment of use while simultaneously maintaining the integrity of the device and the stability of the fluid-sensitive beneficial agent within the device. The presence of the expandable driving member as a layer over an extensive portion of the vertical walls of the first wall section according to the invention provides substantially less ingress of fluid into the fluid-sensitive beneficial agent formulation and substantially less breakage and malfunction of the delivery device, with a resulting greatly improved delivery of the beneficial agent. While there has been described and pointed out features of the invention as applied to presently preferred embodiments, those skilled in the art will appreciate that various modifications, changes, additions and omissions in the devices illustrated and described can be made without departing from the spirit of the invention.

What is claimed is:

1. A fluid-imbibing delivery device for delivering a beneficial agent to a biological environment of use, the delivery device comprising:
   (a) a rigid housing defining an internal compartment, the housing comprising
      (i) a first wall section having either an osmotic permeability coefficient less than about $3.7 \times 10^{-7}$ cm.mil/atm.hr or a water vapor transmission rate less than about 11 g.mil/100 in$^2$/24 hr at 38° C., having an open end;
      (ii) a second wall section permeable to fluid in the environment of use, the second wall section surrounding at lease a portion of the first wall section in spaced apart relationship thereto and enclosing the open end thereof, the second wall section being in sealing relationship around the periphery of the first wall section at a location distal to the open end thereof; and
      (iii) exit means providing fluid communication between the environment of use and the portion of the compartment within the first wall section distal to the open end;
   (b) a fluid swellable driving member in the space between the first and second wall sections and in communication with the open end; and
   (c) a beneficial agent formulation in the internal compartment adjacent to the exit means.

2. A delivery device according to claim 1, wherein at least one-half of a length of the first wall section is surrounded by the fluid swellable driving member and the second wall section.

3. A fluid-imbibing delivery device for delivering a beneficial agent to a biological environment of use, the delivery device comprising:
   (a) a rigid housing enclosing an internal compartment, the housing having
      (i) a shape-retaining first wall section, wherein said first wall section has either an osmotic permeability coefficient less than about $3.7 \times 10^{-7}$ cm.mil/atm.hr or a water vapor transmission rate less than about 11 g.mil/100 in$^2$/24 hr at 38° C., having exit means and an open end, the first wall section defining the internal compartment;
      (ii) an osmotically active expandable driving member surrounding at least about one-half of the vertical sides of the first wall section and enclosing said open end; and
      (iii) a fluid-permeable second wall section surrounding and enclosing the expandable driving member; and (b) a beneficial agent formulation in a portion of the internal compartment adjacent to the exit means.

4. A delivery device according to claim 1 further including a fluid-impermeable partition layer between the beneficial agent formulation and the expandable driving member.

5. A delivery device according to claim 1 wherein the expandable driving member surrounds at least two-thirds of the length of the first wall section.

6. A delivery device according to claim 1 wherein the environment of use is an animal.

7. A delivery device according to claim 6 wherein the animal is a swine or a bovine.

8. A delivery device according to claim 1 wherein the beneficial agent is a hormone.

9. A delivery device according to claim 1 wherein the beneficial agent is a somatotropin or a somatotropin analogue.

10. A delivery device according to claim 1 wherein the device is an implant.

11. A delivery device according to claim 1 wherein the exit means comprises an exit passageway and means for closing the exit passageway.

12. A delivery device according to claim 11 wherein the means for closing the exit passageway is a material which is discharged, leaches or erodes.

13. A delivery device according to claim 1 wherein the driving member comprises an osmagent or an osmopolymer together with an osmagent.

14. A delivery device according to claim 10 wherein the beneficial agent is a somatotropin or a somatotropin analogue, and the fluid swellable driving member comprises and osmagent or an osmopolymer together with an osmagent.

* * * * *